(12) United States Patent
Richter et al.

(10) Patent No.: US 10,667,909 B2
(45) Date of Patent: Jun. 2, 2020

(54) INVERTING TEMPORARY VALVE SHEATH

(71) Applicant: VALVE MEDICAL LTD., Tel Aviv (IL)

(72) Inventors: Yoram Richter, Ramat Hasharon (IL); Ety Weisz, Tel Aviv (IL); Mark Kreizer, Yavne (IL)

(73) Assignee: Valve Medical Ltd., Tel Aviv (IL)

( * ) Notice: Subject to any disclaimer, the term of this patent is extended or adjusted under 35 U.S.C. 154(b) by 310 days.

(21) Appl. No.: 15/593,484

(22) Filed: May 12, 2017

(65) Prior Publication Data
US 2017/0325955 A1    Nov. 16, 2017

Related U.S. Application Data

(60) Provisional application No. 62/336,983, filed on May 16, 2016.

(51) Int. Cl.
*A61F 2/24* (2006.01)
*A61F 2/95* (2013.01)

(52) U.S. Cl.
CPC .......... *A61F 2/2439* (2013.01); *A61F 2/2412* (2013.01); *A61F 2/2427* (2013.01);
(Continued)

(58) Field of Classification Search
CPC .......... A61F 2/013; A61F 2/24; A61F 2/2412; A61F 2/2427; A61F 2/2436;
(Continued)

(56) References Cited

U.S. PATENT DOCUMENTS 3,671,979 A    6/1972  Moulopoulos
4,009,717 A    3/1977  Allen
(Continued)

FOREIGN PATENT DOCUMENTS

JP    H6-83040       11/1994
JP    2001-503286    3/2001
(Continued)

OTHER PUBLICATIONS

Partial International Search Report and Invitation to Pay Additional Fees dated Aug. 22, 2017 for PCT Application No. PCT/IB2017/000630, 15 pages.
Notice of International Preliminary Report on Patentability for PCT Application No. PCT/IB2014/001564 dated Sep. 24, 2015, 9 pages.
Salizzoni et al., "Transapical Off-Pump Removal of the Native Aortic Valve: A Proof-of-Concept Animal Study," The Journal of Thoracic and Cardiovascular Surgery, Aug. 2009, vol. 138, Nov. 2: 468-73.
(Continued)

*Primary Examiner* — Robert A Lynch
(74) *Attorney, Agent, or Firm* — Cadwalader, Wickersham & Taft LLP (57) ABSTRACT

A percutaneous device including a temporary valve attached to a sheath, the sheath having an inverting section for delivery and removal thereof from a blood vessel. The sheath is inverted for delivery, housing the valve between inverted layers thereof. To deploy said valve, the sheath is everted to position the temporary valve on an outer surface thereof. The temporary valve and sheath are reversibly movable between inverted and deployed configurations. Upon eversion, the temporary valve assumes a radially expanded canopy shape having an outer diameter selected to contact the vessel wall and allow blood flow in only one direction. The temporary valve may be removed by releasing one end of the valve from the sheath, flattening the temporary valve along the longitudinal axis of the sheath. Also provided is a temporary valve system comprising a dilator for inverting and everting the sheath, said dilator being removably connected to the sheath.

50 Claims, 9 Drawing Sheets

(52) U.S. Cl.
CPC .... *A61F 2/2436* (2013.01); *A61F 2002/9528* (2013.01); *A61F 2250/0059* (2013.01)

(58) Field of Classification Search
CPC ........... A61F 2/2439; A61F 2250/0059; A61B 17/1204; A61B 17/12109; A61B 17/12131; A61B 17/12177
See application file for complete search history.

(56) References Cited

U.S. PATENT DOCUMENTS

| | | | |
|---|---|---|---|
| 4,056,854 | A | 11/1977 | Boretos et al. |
| 4,109,659 | A | 8/1978 | Sheridan |
| 6,355,030 | B1 | 3/2002 | Aldrich et al. |
| 7,320,704 | B2 | 1/2008 | Lashinski et al. |
| 8,784,480 | B2 | 7/2014 | Taylor et al. |
| 2005/0010285 | A1 | 1/2005 | Lambrecht |
| 2005/0240200 | A1 | 10/2005 | Bergheim |
| 2005/0283231 | A1 | 12/2005 | Haug et al. |
| 2007/0149996 | A1 | 6/2007 | Coughlin |
| 2007/0255394 | A1 | 11/2007 | Ryan |
| 2009/0222082 | A1 | 9/2009 | Lock et al. |
| 2010/0179583 | A1 | 7/2010 | Carpenter et al. |
| 2010/0179585 | A1 | 7/2010 | Carpenter et al. |
| 2011/0152760 | A1 | 6/2011 | Parker |
| 2011/0295304 | A1 | 12/2011 | Jonsson |
| 2012/0116351 | A1 | 5/2012 | Chomas et al. |
| 2014/0277096 | A1 | 9/2014 | Richter et al. |
| 2014/0309732 | A1 | 10/2014 | Solem |
| 2014/0350523 | A1 | 11/2014 | Dehdashtian et al. |
| 2017/0119517 | A1 | 5/2017 | Pain et al. |

FOREIGN PATENT DOCUMENTS

| | | |
|---|---|---|
| JP | 2012-085816 | 5/2012 |
| JP | 2016-510616 | 4/2016 |
| RU | 2556545 | 7/2015 |
| SU | 1424810 | 9/1988 |
| WO | WO 97/48436 | 12/1997 |
| WO | WO 00/44313 A1 | 8/2000 |
| WO | WO 2011/130093 A1 | 10/2011 |
| WO | WO 2014/177935 A2 | 11/2014 |
| WO | WO 2014/177935 A3 | 11/2014 |
| WO | WO 2015/185870 | 12/2015 |

OTHER PUBLICATIONS

Extended European Search Report dated May 15, 2018 for EP application No. 18201500.8.
International Search Report and Written Opinion dated Nov. 17, 2017 for PCT Appl. No. PCT/IB2017/000630, 21 pages.
Russian Search Report for Application No. 2018144119 dated Jun. 20, 2019, 4 pages.
Russian Search Report for Application No. 2018145775 dated Jul. 31, 2019, 4 pages.

INVERTING TEMPORARY VALVE SHEATH

This application claims the benefit of priority of U.S. Provisional Application Ser. No. 62/336,983 filed May 16, 2016.

FIELD OF THE INVENTION

The present invention relates to a temporary valve and sheath for maintaining normal blood flow during percutaneous cardiovascular procedures. The invention also relates to a system comprising an inverting temporary valve device, a method of deploying said device in a living body and a method of removing said device from the body.

BACKGROUND OF THE INVENTION

Valves are important structures in the human heart because they maintain blood flow in a single direction with minimal pressure loss. However, human heart valves can degenerate for a variety of reasons. For example, a malfunctioning heart valve may be stenotic, where the leaflets of the valve do not open fully, or the valve may be regurgitant, where the leaflets of the valve do not close properly, or a combination of both. Valve repair and replacement procedures have thus been developed to either restore the function of the native valves or to implant a permanent prosthetic valve with or without removal of the original native valve. The standard surgical procedure involves the opening of the patient's thoracic cavity, which is highly invasive and requires cardiopulmonary bypass and a prolonged recovery time.

Percutaneous valve repair and replacement procedures have been developed as cheaper and safer substitutes for traditional open chest surgeries. Compared to traditional surgery, a percutaneous valve repair procedure is minimally invasive and eliminates the need for cardiopulmonary bypass. In the absence of cardiopulmonary bypass, the percutaneous procedure must take place quickly to restore normal circulation, because native valve function is interrupted during the repair or the positioning and implantation of the permanent prosthetic valve. A temporary valve is a useful tool to, in one respect, maintain unidirectional blood flow during the percutaneous procedure before the permanent prosthetic valve is implanted and/or operational. Further, a temporary valve may be useful during a balloon aortic valvuloplasty (BAV) procedure in which the native valve is dilated with a balloon and which occasionally causes harm to one or more of the native valve leaflets. The temporary valve may serve to replace the function of the one or more native valve leaflets damaged during the BAV procedure. BAV procedures may be stand-alone (e.g., in which no prosthesis is implanted) or may precede percutaneous prosthetic valve implantations either immediately or by a period of several hours, days or weeks.

Therefore, a need exists for a device that can maintain blood flow in a single direction during, e.g., a percutaneous valve repair or replacement procedure and may be removed without causing trauma to the vessel or unduly increasing the time or effort needed to complete the procedure.

SUMMARY OF THE INVENTION

The invention relates to a device comprising a percutaneous temporary valve and sheath having an inverting section for delivery and removal of the percutaneous temporary valve from a target blood vessel. The invention also relates to a percutaneous temporary valve system and method of deployment. The device may be used in percutaneous valve repair procedures, valve replacement procedure or any situation in which native valve function is insufficient. The device may be removed without causing trauma to the vessel or unduly increasing the time or effort needed to complete the procedure. The device may provide temporary hemodynamic support to a patient for various periods of time lasting from seconds to hours and possibly days.

The invention provides a temporary percutaneous valve device, comprising a sheath having a first section located distally of a second section, said first section having a temporary valve attached thereto. In one embodiment, the first section may be formed of a plurality of braided members (e.g., fibers, wires, etc.). The first section is inverted for delivery, housing the valve between inverted layers thereof. In the inverted configuration, at least a portion of the first section is turned or folded into itself, with the valve situated between layers of the first section, such that all or part of the first section extends into a luminal portion of the second section. To deploy said temporary valve at a target site, the first section is everted to position the temporary valve on an outer surface thereof. The temporary valve and first section are reversibly movable between said inverted configuration and a deployed configuration, wherein, during deployment, said first section is moved distally out of said sheath channel. Upon eversion, the temporary valve assumes a radially expanded canopy shape having an outer diameter selected to contact the vessel wall and allow blood flow in only one direction, e.g., away from the heart, for example during systole. The temporary valve may be held in its canopy shape by a plurality of lines connecting the outer diameter of the valve to the first section. Alternatively, the plurality of lines may connect the outer diameter of the valve to the second section.

The invention also relates to a temporary percutaneous valve system comprising a dilator used for inverting and everting the sheath. The dilator is received through said sheath and includes first and second wires coupling the dilator to the sheath such that proximal movement of the dilator relative to the sheath causes the first section to be inverted and distal movement of the dilator relative to the sheath causes the first section to be everted. The connection between the dilator and sheath is removable, thus allowing the dilator to be withdrawn from the system upon deployment of the temporary valve.

The invention also relates to a method for removing the deployed temporary valve from a vessel. In one embodiment, the lines of the temporary valve may be disconnected from the sheath, said disconnection permitting the canopy of the temporary valve to move to a substantially tubular configuration, e.g., by everting. Once disconnected, the valve device, including the sheath and temporary valve may be withdrawn from the body. In another embodiment, the temporary valve and sheath may be withdrawn from the body without inverting. In yet another embodiment, the temporary valve may be inverted into the sheath for withdrawal from the body. In this embodiment, the inversion may be carried out via a third wire which extends through a lumen of the dilator and out of a distal end of the dilator to loop about a portion of the first section of the sheath containing the temporary valve, connecting the temporary valve and sheath to the third wire. A proximal end of the third wire remains outside of the dilator and is accessible by a surgeon. During removal, the surgeon pulls the third wire proximally to invert the first section proximally into the second section. The inverted sheath and valve have a reduced outer profile and can be removed from the vessel.

The system and method disclosed herein is adapted for use in surgical methods including, but not limited to, open surgical procedures, percutaneous procedures, minimally-invasive procedures, trans-catheter procedures, direct-entry procedures, endoscopic procedures, and the like, as those skilled in the art will understand. Although the systems and methods disclosed herein are described with respect to a percutaneous procedure, any other approach may be used without deviating from the scope of the invention.

DETAILED DESCRIPTION OF THE INVENTION

The invention relates to an inverting sheath and an integrated percutaneous temporary valve for use in intraluminal procedures. The invention also describes a method of delivery and deployment of a percutaneous temporary valve system and methods for its removal.

Device

A device according to the invention comprises a sheath having a first section located distally of a second section, said first section having a temporary valve attached thereto. In an embodiment of the invention, a first end of the temporary valve is permanently attached to the first section and a second end of the temporary valve is removably attached to the first section by a plurality of lines. In one embodiment, the first section and temporary valve are movable between an inverted or partially inverted configuration for delivery and a radially expanded canopy or umbrella configuration after deployment. Expansion of the canopy from the inverted configuration may be aided by optional ribs in the valve body. A package or kit according to the invention further comprises a catheter or other similar known intraluminal delivery instrument.

The device may be used with a dilator insertable through the sheath. The dilator, which aids in intravascular access, delivery and deployment, also controls inversion and expansion of the temporary valve. The dilator is removably coupled to the temporary valve and sheath via first and second wires. As the dilator slides proximally and distally through the sheath, a connection of the first and second wires to the temporary valve and first section causes a corresponding inversion and/or eversion of the first section. Specifically, the first wire extends through a lumen of the dilator and out of a distal end of the dilator to loop about a portion of the first section of the sheath containing the temporary valve, connecting the temporary valve and sheath to the dilator. A proximal end of the first wire remains outside of the dilator and is accessible to a surgeon.

Delivery and Deployment

The sheath is inverted prior to delivery to house the valve between inverted layers of the sheath in the inverted configuration within the guide tube. To deploy said temporary valve at a target site, the first section is everted to permit a radial expansion of the temporary valve and position the temporary valve on an outer surface thereof. Upon deployment, the temporary valve assumes a radially expanded canopy shape having an outer diameter and allows blood flow in only one direction, i.e., during systole. As used herein, the term deliver refers to a delivery of the sheath or other device components from outside the body to a selected intravascular location. The term deployment, as used herein, refers to a configuration in which the dilator is pushed distally, expelling and everting the first section of the sheath and causing an expansion (i.e., deployment) of the temporary valve. In one embodiment, radial expansion of the canopy from the inverted configuration may be aided by optional ribs in the valve body, said ribs having a structural rigidity to automatically assume a canopy configuration independent of blood flow through the vessel. The temporary valve is held in the canopy shape by optional lines, which may connect at one end to attachment points on the first section of the sheath and at the other end to the perimeter of the valve canopy. As blood flows through the vessel in a first direction during systole, the blood applies a pressure to an outer surface of the canopy, causing radial compression thereof and allowing flow therepast. As blood flows in an opposite second direction during diastole, the blood applies pressure to an inner surface of the canopy, causing radial expansion thereof to effectively impede blood flow through the vessel. Thus, in the canopy configuration, the temporary valve allows blood flow in only one direction, i.e. during systole. A permissible volume of blood may move past the temporary valve during diastole, e.g., between an outer perimeter of the canopy and the vessel wall and/or through a lumen of the temporary valve. However, the volume of this blood flow is small and still permits maintenance of unidirectional blood flow through the vessel. The valve device thus permits continued functionally unidirectional blood flow through a target vessel during a target procedure, even in the absence of a native valve and/or the presence of a non-functional or partially functional native valve.

Inversion and radial expansion of the temporary valve and sheath during delivery and deployment is controlled by movement of the dilator within the sheath; that is, resulting in an inversion of the temporary valve and sheath when proximal movement of the dilator occurs and resulting in eversion and radial expansion of the temporary valve when distal movement occurs. The term proximal, as used herein, refers to a direction toward a hub of the sheath (i.e., in the direction of blood flow during systole and the term distal refers to a direction opposite the proximal direction (i.e., toward the target treatment site)). Once the temporary valve has been deployed at a target position in the vessel, the first wire is pulled out of the device, disconnecting the dilator from the sheath and permitting withdrawal of the dilator proximally of the sheath while the temporary valve and sheath remain in the vessel.

Removal from the Body

The temporary valve of the invention may be used to control the heart's blood flow during various surgical procedures requiring such intervention. For example, a temporary valve may be needed before, during or after surgical procedures (e.g., during preparation for a surgical procedure) such as a valve replacement, valve repair or other heart surgeries. Once the procedure is completed, the valve and sheath may be removed from the body in one of a number of ways. In one embodiment, a portion of the temporary valve may be detached from the first section of the sheath by releasing the lines to reduce an outer profile of the valve, the detachment permitting the canopy of the valve to move to an elongated, substantially straightened tubular configuration (an everted position) or any shape permitting easier removal from the body. Specifically, only a portion of the temporary valve is detached from the sheath in the detached configuration. A first end of the temporary valve remains permanently attached to the sheath while a second, opposite end is reversibly connected to said sheath. The permanently attached first end of the temporary valve forms a continuous sheet or canopy of the temporary valve. This detachment of the second end may also serve to reduce friction encountered during the procedure and/or change the shape of the temporary valve, as described in greater detail with respect to FIGS. 1-8 below. Specifically, an attachment wire connecting the lines to the first section of the sheath may be withdrawn proximally, thereby releasing a connection between the lines and first section. This release allows the valve body to assume a reduced outer profile by, for example, straightening, everting or otherwise shifting position or shape. Once detached, the device, including the first section and temporary valve may be withdrawn from the body. In another embodiment, the temporary valve and sheath may be withdrawn from the body without everting. Specifically, the flexible materials of the temporary valve allow for removal thereof from the body without causing undue trauma to the vessel. In yet another embodiment, the temporary valve may be inverted for withdrawal from the body, said inversion being carried out via a third wire and being independent of the position of the dilator within the sheath. The third wire extends through a lumen of the dilator and out of a distal end of the dilator to loop about a portion of the first section containing the temporary valve, connecting the temporary valve and first section to the third wire. The proximal end of the third wire remains outside of the dilator and is accessible by a surgeon. During removal, the surgeon pulls the third wire proximally to move the first section of the sheath proximally. The second section remains stationary such that the proximal movement of the first section causes inversion of the first section and temporary valve into the second section. The inverted first section and valve have a reduced outer profile and can be removed from the vessel.

Figure 1:
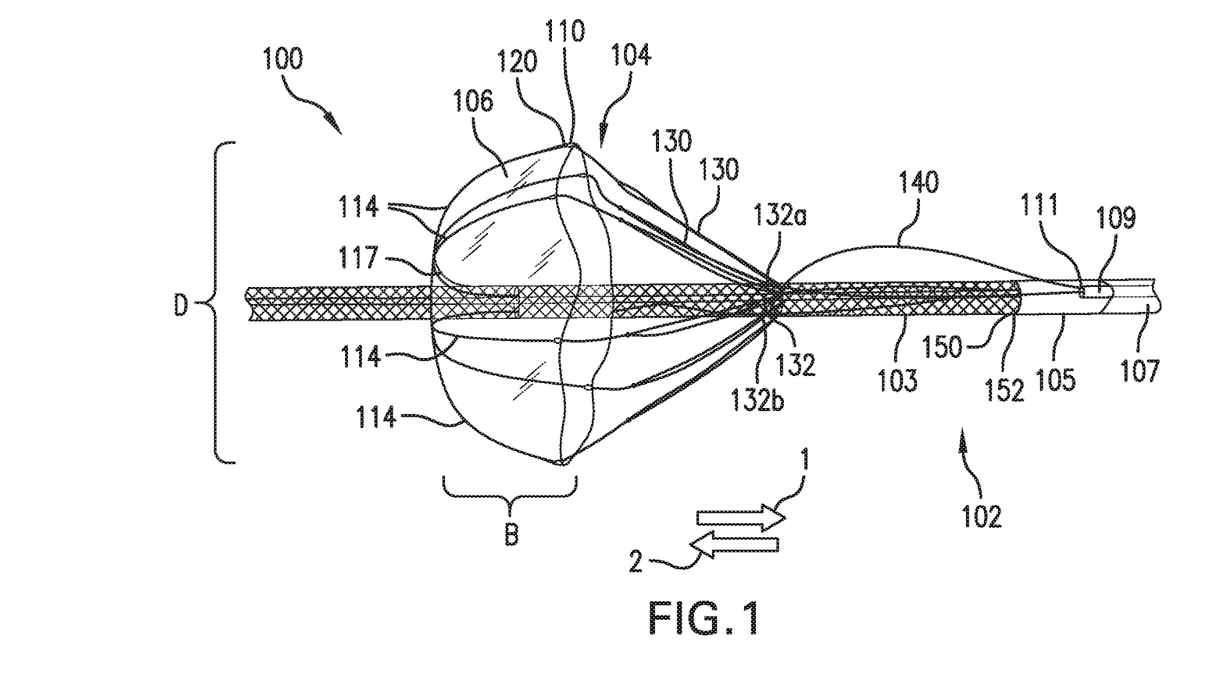
FIG. 1 illustrates a sheath and temporary valve according to a first embodiment of the invention in a radially expanded canopy configuration.
Figure 3:
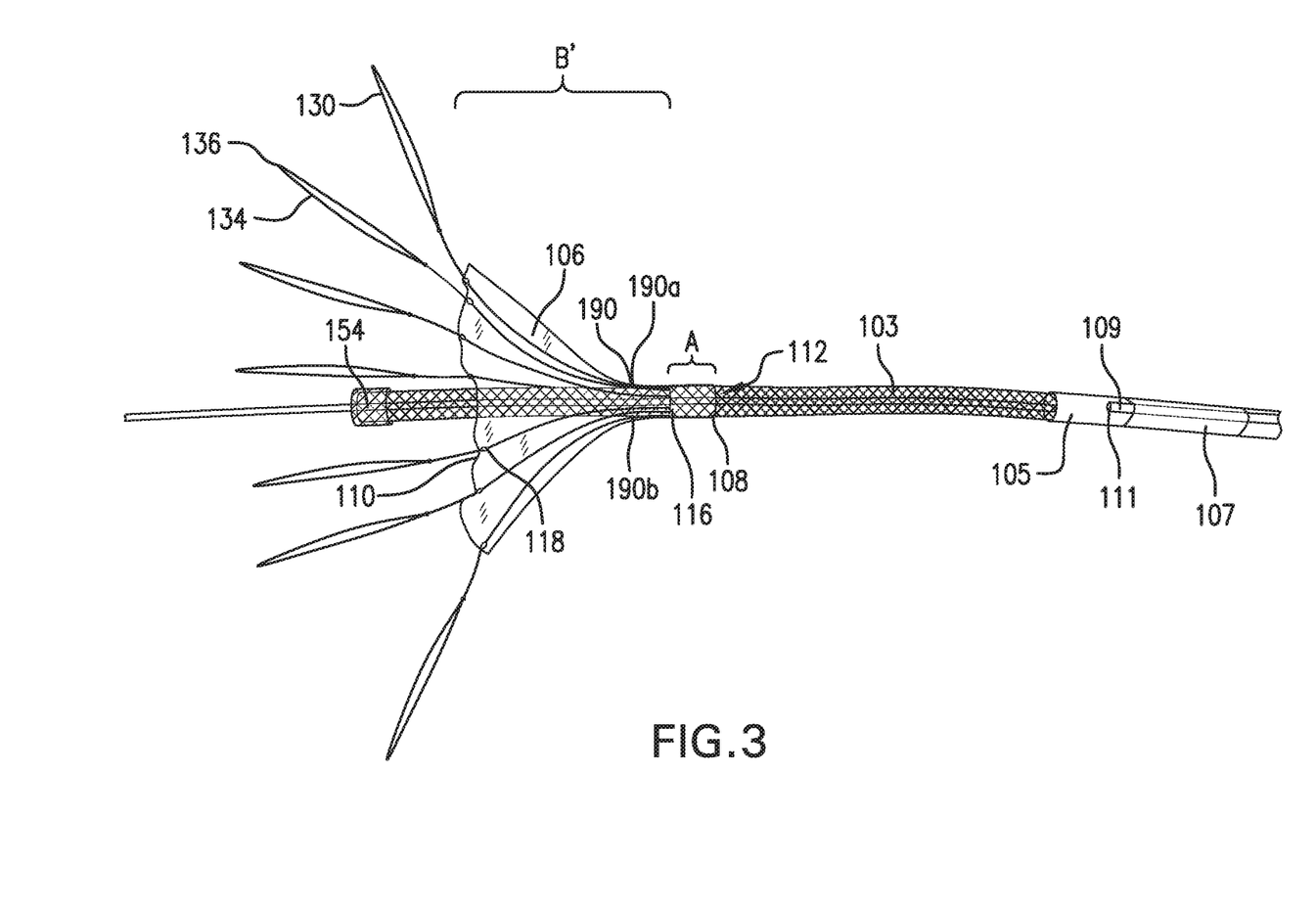
FIG. 3 illustrates the sheath and temporary valve of FIG. 1 in an everted configuration.
Figure 4:
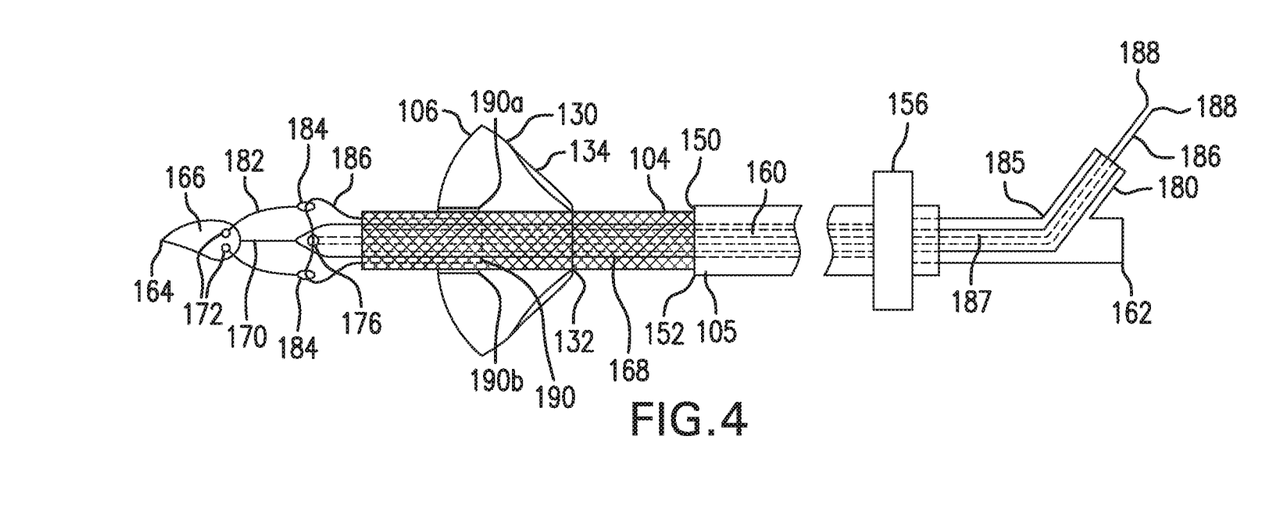
FIG. 4 illustrates a partial cross-sectional view of the sheath and temporary valve of FIG. 1 in a deployed configuration.
Figure 5:
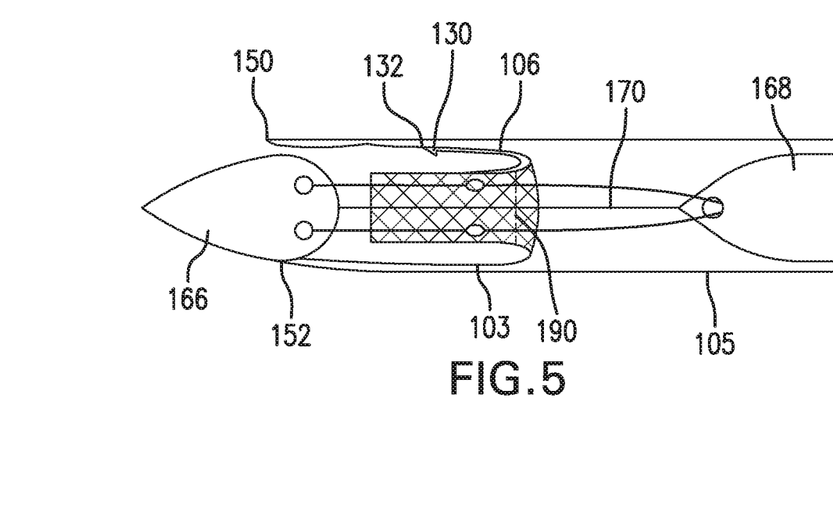
FIG. 5 illustrates a partial cross-sectional view of the sheath and temporary valve of FIG. 1 in an inverted insertion configuration.

FIGS. 1-8 illustrate a percutaneous temporary valve device according to the invention. One embodiment of the invention, shown in FIG. 1 illustrates temporary valve device 100 which comprises a delivery device 102 and a temporary valve body 104. The delivery device 102 includes a sheath 101 having a first section 103, second section 105 and optional outer tube 107. The temporary valve body 104 is movable between the deployed radially expanded canopy shaped configuration of FIG. 1 and an inverted insertion configuration, as depicted in FIG. 5. The temporary valve body 104 has an elongated tubular valve canopy 106 extending from a first end 108 to a second end 110. A lumen 112 extends through the temporary valve body 104, the lumen being sized to receive the sheath first section 103 therethrough, the first section 103 further being sized to slidably receive a catheter shaft (not shown) therethrough. In one embodiment, the temporary valve device may have a pre-deployment length of 54 cm and a post-deployment length of 62 cm.

As depicted in FIG. 1, an outer perimeter of the tubular valve canopy 106 forms an umbrella or parachute shape. A diameter of the valve canopy 106 at region A is uniform or substantially uniform and closely matches an outer diameter of the first section 103. The temporary valve 104 further comprises a region B forming an outer perimeter of the canopy. As depicted in FIG. 1, region B represents a radially expanded canopy configuration of the valve canopy 106 and may have a length of approximately 25 mm. Region B', as depicted in the example of FIG. 3, representing a straightened or everted configuration of the valve canopy may have a length of 45-50 mm. Alternatively, the region B' may have a length in the range of 10-100 mm. The outer perimeter of the canopy abuts the vessel wall whereas the first end 108 of the valve body 104 is secured to the first section 103. Dimensions of the valve canopy 106 are selected so that a maximum outer diameter D of the valve canopy 106 in the deployed umbrella-shaped configuration is selected to closely match a diameter of a vessel within which the valve device 100 is implanted. For example, the maximum outer diameter of the deployed valve canopy 106 may be 20-30 mm or 35 mm although larger and smaller diameters are envisioned to permit use of the device 100 in larger or smaller vessels, respectively. Preferably, the maximum outer diameter of the deployed valve canopy 106 substantially matches or is slightly larger than a diameter of a vessel in which the valve body 104 is to be implanted. For example, a maximum outer diameter of the deployed valve canopy 106 may be 6-10 mm, or 8 mm when used in a femoral artery and approximately 14-30 mm, 18 mm, 20-30 mm or 45 mm when used in a proximal descending aorta. In a preferred embodiment, an unconstrained diameter of the valve canopy may be 45 mm or anywhere in the range of 10-80 mm. The unconstrained diameter of the valve canopy 106 may be selected to match the diameter of the vessel in which the valve canopy 106 is inserted or may be larger than the diameter of said vessel. For example, the vessel diameter to valve canopy diameter ratio may be from 1:1 to 1:5. In one embodiment, the ratio is 1:2. The above dimensions are exemplary only and any other diameter appropriate for a particular vessel may be employed herein without deviating from the scope of the invention.

In one embodiment, a plurality of ribs 114 may be provided and evenly distributed about a circumference of the valve canopy 106, the ribs extending from first ends 116 to second ends 118. The ribs 114 structurally reinforce the valve canopy 106 and define a shape thereof. That is, in the deployed position illustrated e.g. in FIG. 1, the ribs 114 maintain the valve canopy structure to hold an open umbrella-shaped position, even in the absence of blood flow. The ribs 114 may be attached to an inner or outer surface of the valve canopy 106. In another embodiment, the ribs 114 may be embedded in the material of the valve canopy 106.

In a preferred embodiment, the device 100 includes preferably 4-12 ribs, more preferably eight ribs 114, although a greater or lesser number of ribs 114 may be used without deviating from the scope of the invention. The number of ribs may range from 2-20 or 6-15. In another embodiment, the device may include sixteen ribs. The number of ribs is selected to provide a balance of structural rigidity while still permitting the valve canopy 106 to fold and unfold easily. The ribs are preferably evenly spaced about the circumference of the canopy. The first ends 116 of the ribs are axially separated from the first end 108 of the valve canopy 106 by a predetermined distance around the circumference of the first section, denoted by region A of FIG. 1. The ribs extend from an end of the region A to the second end of the valve body 110. Region A comprises a glue or polymer as known in the art to secure the first end 108 of the valve body (and optionally the ribs 114) to the first section 103. Alternatively, the region A may be omitted and the proximal end of the region B may be secured directly to the first section 103. As depicted in FIG. 1, during systole, blood flows in the direction 1 and applies a pressure to an outer surface 117 of the temporary valve, causing the valve canopy 106 to partially compress and allow blood flow therepast. During diastole, blood flows in the direction 2 and applies a pressure to the inner surface 119 of the temporary valve body 104, thereby preventing blood from flowing past the canopy 106 due to engagement with the inner surface of the valve canopy 106.

The second end 118 of each of the ribs 114 may optionally include a ring 120 permitting attachment of lines 130 thereto. The lines 130 secure the ribs 114 or, in an embodiment where the ribs 114 are omitted, an edge of the valve body 104 to the first section 103 at a position proximal to the valve canopy 106. This attachment position is exemplary only and other attachment positions may be used without deviating from the scope of the invention. For example, lines 130 may be connected to the valve body 104 or distal thereto or to the second section 105. The rings 120 are formed as a loop of the same material as the ribs 114, although other materials are also envisioned. The rings 120 may be unitary with the ribs 114 or, in another embodiment, may be separate elements attached thereto via welding or another attachment means known in the art. In yet another embodiment, the lines 130 may be attached to the ribs 114 by an attachment mechanism other than rings (e.g., gluing, welding, etc.). The second ends 118 of the ribs may be separated from the second end 110 of the valve canopy 106 by a gap. The length of the gap may be selected to prevent free or sharp edges of the ribs 114 from coming into contact with luminal tissue. The length of the valve canopy 106 in the gap may be scrunched or gathered when a line 130 is attached to the ring 120. In another embodiment (not shown), the second end of the ribs 114 may extend to a distal edge of the valve canopy 106 without the gap. In yet another embodiment, the ribs may extend beyond the second end of the valve body, wherein the second end of the ribs connects directly to the first section without the use of lines 130.

In another embodiment (not shown), the device 100 may be formed without ribs 114. In this embodiment, the valve canopy 106 may include one or more radiopaque markers disposed on, under or embedded therein. Further, lines 130 may be secured directly to the valve canopy material (e.g., knotted to openings formed through the valve canopy, formed integrally with the valve canopy 106, formed as extensions of the valve body material, etc.).

The plurality of lines 130 connect the temporary valve body 104 to the first section 103. Each of the plurality of lines 130 is knotted or otherwise secured to the valve canopy at a second end and secured to the first section 103 at a first end to an attachment area located proximal of the first end 108 of the temporary valve body 104. As noted earlier, the plurality of lines are not necessarily located proximal of the valve body 104 and may be located on the valve body 104 or distal thereto. Each of the lines 130 may include a loop, hook or other attachment element at a free end to permit weaving or other reversible connection to an attachment wire 140. Loops 134 may extend for a portion of or the entire length of the lines 130. Each of the lines 130 may have approximately the same length or alternatively, the lines 130 may have a combination of long and short lengths, said length(s) being selected to maintain the valve canopy shape when deployed in the vessel wall. Free ends 136 of lines 130 are positioned circumferentially about the first section 103 at the attachment point 132 and connected thereto via the attachment wire 140. The attachment wire 140 extends through delivery device 102 from the proximal opening toward the attachment area 132 and is sequentially interwoven with each of the loops, hooks or other attachment elements and an adjacent opening of the first section 103 to secure the loops to the first section 103. As such, the attachment wire secures the lines 130 at the attachment point in a manner to form a reversible attachment between the valve and sheath 101. In an alternative embodiment, the attachment wire 140 may be replaced by a string, removable pin or other attachment mechanism.

During manufacture of the device, the attachment wire 140 is passed through the braiding of the first section 103 at attachment point 132a, is sequentially woven through respective loops, hooks or other attachment elements and openings in the first section about said first section circumference and subsequently extends outside the first section 103 at attachment point 132b. In another embodiment, the attachment wire 140 extends inside the first section 103 at attachment point 132b, the attachment wire 140 being housed within the first section 103. In one embodiment the attachment wire 140 extends 180 degrees about the first section 103 at the attachment point 132b. In other configurations the attachment wire is woven about all of some portion of the circumference of the first section, e.g., 90 degrees, 180 degrees, 270 degrees or e.g. 360 degrees. The first free end of the attachment wire 140 is then woven back into the lumen of the delivery device 102 and out of the proximal end thereof (not shown) so that both first and second free ends of the attachment wire 140 are located at the proximal end of the delivery device, accessible to the operator.

Figure 2:
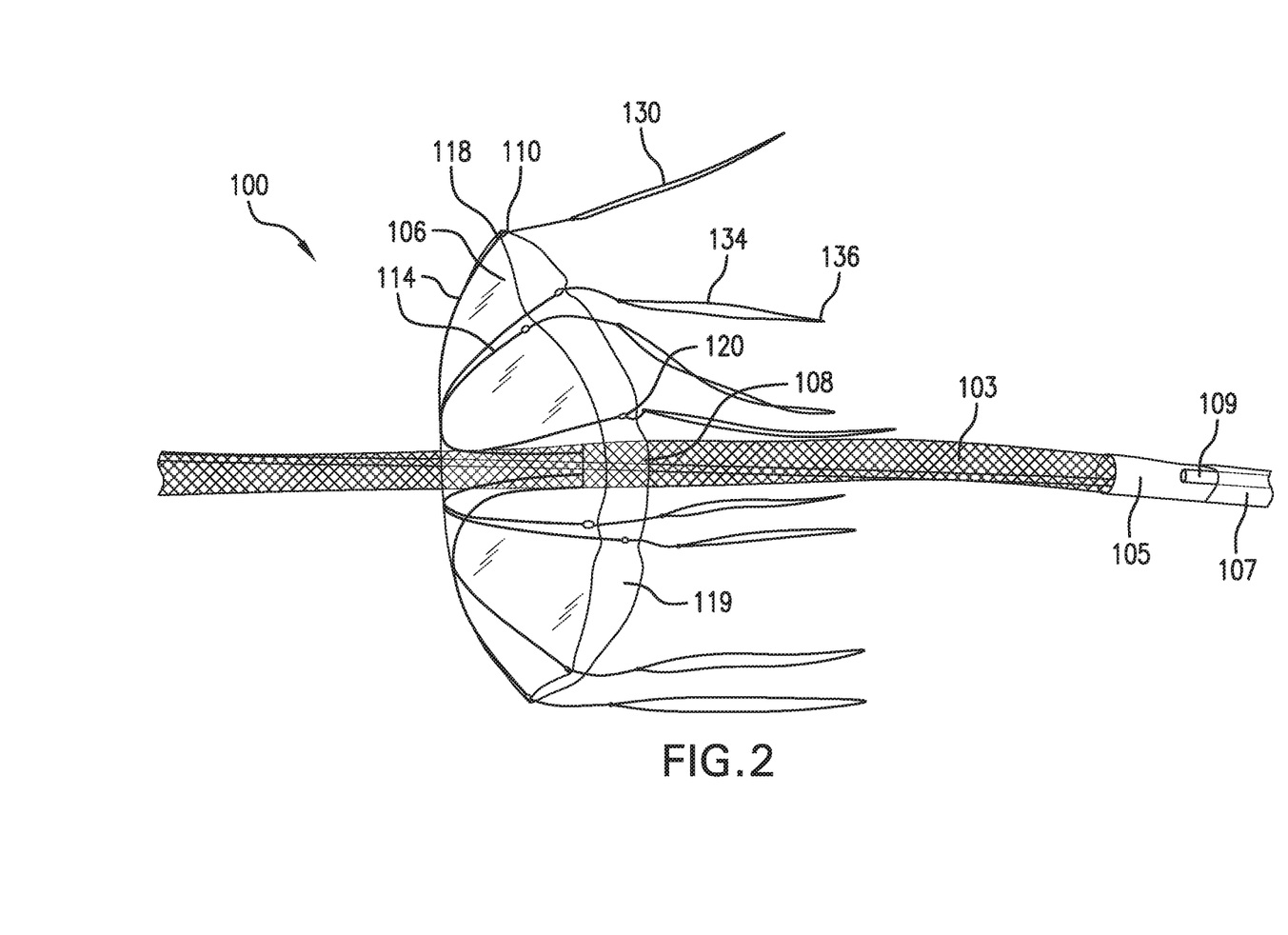
FIG. 2 illustrates the sheath and temporary valve of FIG. 1 during a detached configuration.

Once use of the temporary valve is completed, the invention further comprises a method of removing the temporary valve comprising, in one embodiment, releasing one of the first and second free ends of the attachment wire 140 and retracting the attachment wire 140 from the body, thereby releasing the lines 130 from the attachment wire. This release, or detachment, permits the valve canopy to be opened and straightened to a reduced outer circumference, as shown in the everted configuration of FIG. 3, thereby facilitating removal thereof from the body while minimizing or preventing trauma to the vessel wall. The valve body and the optional ribs straighten, becoming aligned along the length of the first section (as shown in FIG. 2 and FIG. 3). The first section 103 may be secured at its proximal end 150 to the distal end 152 of the second section 105 via an attachment means known in the art such as e.g., thermal bonding, glue, or the like. The first section 103 and second section 105 may be connected to one another by a means known in the art, such as for example a contiguous configuration. In an alternative embodiment, the first and second sections 103, 105 may overlap at their junction. A distal end 154 of the first section 103 of the sheath 101 may optionally be sealed using a cuff or other sealant to prevent the free ends of the braid from unwinding, as one of skill in the art will understand. Alternatively, the distal end 154 may be sealed against unwinding by one or more of gluing to a polymer, sewing, molding or another sealing option known in the art. In an alternate embodiment, the first section 103 may be manufactured via a closed braid technique wherein the braid does not include sharp free ends at a distal end and is not prone to unwinding, as those of skill in the art will understand.

As depicted in the partial cross-sectional view in FIG. 4, the second section 105 has a diameter slightly larger than a diameter of the first section 103 to permit slidable movement of the first section 103 therethrough. A proximal end of the second section 105 includes a hemostatic valve 156 which prevents blood backsplash, as those of skill in the art understand. The second section 105 has an internal diameter of 6-24 French and an outer diameter of 8-30 French. In one embodiment, the internal diameter of the second section 105 is 12 French and the outer diameter is 14 French or approximately 5 mm. These values are exemplary only and may be modified to conform to the dimensions of a target vessel through which the device 100 is to be inserted and/or the dimensions of a treatment device that needs to pass through the device 100.

The first section 103 may be formed with any diameter sufficiently large to permit a replacement valve, balloon or other device to be inserted therethrough. In one embodiment where the device is being delivered via a catheter having a diameter of 5 mm, the first section 103 may also have a diameter of 5 mm. In a preferred embodiment, the first section 103 diameter may range from 2-9 mm, although smaller or larger dimensions may be used without deviating from the scope of the invention to address the requirements of a particular procedure and/or treatment location, as those of skill in the art will understand. The first section 103 may have a length in the range of 2-20 cm and preferably 10 cm. In a preferred embodiment, the temporary valve 104 is positioned 2.5 cm from the distal end 154 of the first section 103, although any other placement along the first section 103 is envisioned within the scope of the invention. In one alternate embodiment, the temporary valve 104 is positioned at the distal end 154.

Figure 6:
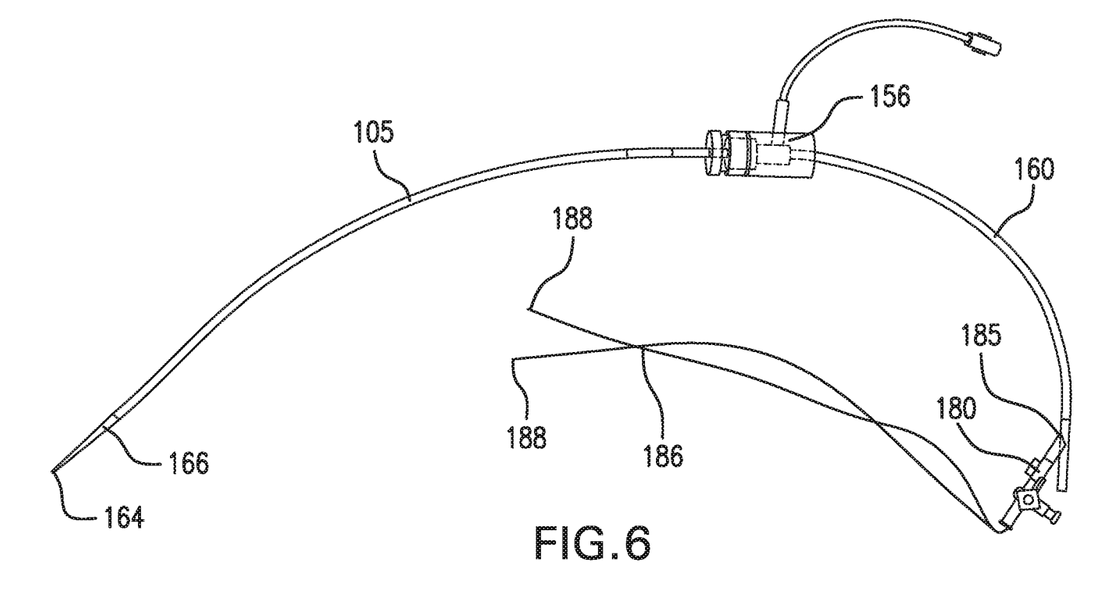
FIG. 6 illustrates a system for delivering and deploying the sheath and temporary valve of FIG. 1.

The delivery device 102 further comprises a dilator 160 extending from a proximal end 162 located outside the body to a distal end 164 having a tip formed as a nosecone 166. The dilator 160 comprises a tubular body, a distal nosecone and a waist therebetween, wherein said dilator aids in dilation of the vessel to facilitate insertion of the device 100 into the body at a target site. The tubular body of the dilator 160 matches or is smaller than an inner diameter of the first section 103 to permit the dilator 160 to be received therethrough. The nosecone 166 may gradually reduce in diameter toward the distal end 164 and may have a conical outer profile. The taper of said nosecone 166 may be linear or exponential. Alternatively, the nosecone may be blunt-ended having no conical or tapered shape but rather be flat-topped, spherical or other shapes. The nosecone 166 is separated from the body 168 of the dilator by a waist 170 which is permanently attached to the tubular body 168 and nosecone 166. The waist 170 has a reduced diameter relative to the nosecone 166 and is configured to form a negative space therearound in which the valve canopy 106 of the valve body 104 is housed in its inverted delivery configuration. Further, although the embodiment of FIGS. 4-5 and 7-9 shows waist 170 having a diameter smaller than the tubular body 168, other configurations are envisioned within the scope of the invention. For example, the tubular body 168 may alternatively be formed with a diameter less than or equal to the waist diameter. The waist 170 may be formed of a rigid, semi-rigid or flexible material. In one embodiment, a diameter of the nosecone 166 may be tapered in the distal direction, as depicted in FIG. 6. In another embodiment, the transition between the nosecone 166 and the waist 170 may not be tapered, as depicted in FIG. 4. The diameter of the dilator body 168 may also be tapered toward the waist 170. In yet another embodiment (not shown), an additional element—e.g., a non-tapered segment—may be provided between the nosecone 166 and the waist 170.

In one embodiment, the nosecone 166 includes openings 172 adapted to receive first wires 182. The first wire 182 includes loops 184 at its respective free ends. The loops 184 may have any length relative to the length of the first wire 182 and are not limited to the dimensions depicted in FIG. 4. The first wire 182 may connect one or more openings in the nosecone to a second wire 186. The length of the first wire 182 may be approximately the length of the waist or twice the length of the waist, although any other length may be used without deviating from the scope of the invention. The first wire 182 comprises a biocompatible material, e.g. Nitinol, polymer or other like biocompatible material. The above embodiment is exemplary only. The first and second wires 182, 186 may be attached to the nosecone 166 in other ways without deviating from the scope of the invention.

The dilator body 168 also includes a distal opening 176 to receive a second wire 186 therethrough (see FIG. 4, e.g.). The second wire 186 may comprise Nitinol wire or polymer having free ends 188 located outside of the body and inserted into the dilator from a proximal end thereof. As shown in FIGS. 4 and 6, a proximal end of the dilator 160 may be fitted with a hub 180 through which the second wire 186 traverses. One end of the second wire 186 is located at the proximal opening 185 at the hub 180 of the dilator 160. The dilator 160 is hollow and includes a central lumen 187 extending therethrough from said proximal opening 185 to said distal opening 176. In one embodiment, the hub may include a locking mechanism (e.g., a knob) to temporarily lock the second wire 186 against movement,—e.g., to prevent unwanted movement of the second wire. The locking mechanism (e.g., the knob) may be unlocked to permit movement of the second wire 186. The second wire 186 traverses the length of the central lumen of the dilator and extends out of the distal opening 176 of the dilator and is sequentially woven through the loops 184 of the first wire 182 to secure the first and second wires to one another. The second wire 186 then extends proximally into the first section 103 toward sheath attachment location 190, between an outer surface of the dilator 160 and an inner surface of said first section 103. The second wire 186 then extends in and out of the first section 103 any plurality of times at the sheath attachment location 190, thereby securing the first section 103 to the dilator 160. Specifically, the second wire 186 exits the first section 103 at attachment point 190*a*, extends 180 degrees about said first section 103 and subsequently extends into the luminal side of the first section 103 at attachment point 190*b*. The second wire 186 then completes a symmetric circuit, extending through the first section 103, into the second one of the loops 184, back into the distal opening 176, through the channel 187 extending out the proximal opening 185 of the dilator. It is noted that although the second wire 186 is described as extending 180 degrees about the first section 103, other configurations may be employed without deviating from the scope of the invention, including approximately 180 degrees, less than 180 degrees or more than 180 degrees.

When the dilator is manually advanced distally in direction 2, the valve body 104 is also advanced distally. Specifically, as the nosecone 166 is advanced in a distal direction, the first and second wires 182 and 186, which couple the dilator to the valve body 104, also move distally. This distal movement facilitates movement of the device from its inverted delivery configuration to a deployed configuration. The dilator 160 may be used to move the valve and first section 103 between the inverted insertion configuration and deployed configuration any plurality of times as needed to perform a procedure.

The method described above is one example of how the dilator 160 may deploy the first section 103 and temporary valve 104. Other deployment methods are within the scope of the invention. In one non-limiting example, the distal end of the dilator body 168 may be used to push the temporary valve 104 out of the first section 103.

The invention further comprises an inverted delivery configuration of the temporary valve system. In an exemplary embodiment, the device 100 is first positioned to an inverted delivery configuration from the radially expanded canopy configuration shown in FIG. 1, an embodiment of which is shown in the partial cross-sectional configuration of FIG. 5. In the inverted delivery configuration, the dilator 160 is retracted proximally in direction 1, i.e., proximally. The dilator 160 is connected to the first section 103 and valve body 104 via the first and second wires 182, 184. Thus, proximal movement of the dilator causes a corresponding proximal movement of the first section 103 and valve body 104. As the dilator 160 is positioned proximally, the first section 103 first becomes compressed, and then inverts, or flips outside in, as shown in FIG. 5. In one embodiment, an overall length of the first section 103 in the inverted delivery configuration is one-half of the length of the first section 103 in the deployed configuration, although other dimensions may be possible depending on the distance the dilator is retracted. In the inverted delivery configuration, the valve body 104 is positioned between two layers of the first section, as shown in FIG. 5. The inverted first section 103 and valve body 104 are housed within the second section 105 in the negative space formed around the waist 170. In the inverted delivery configuration, the nosecone 166 is positioned near the distal end of the second section 105 to facilitate pushable entry thereof into the body and through the vessel, as those skilled in the art will understand. Optionally, the nosecone may be fully retracted into the second section 105.

Figure 7:
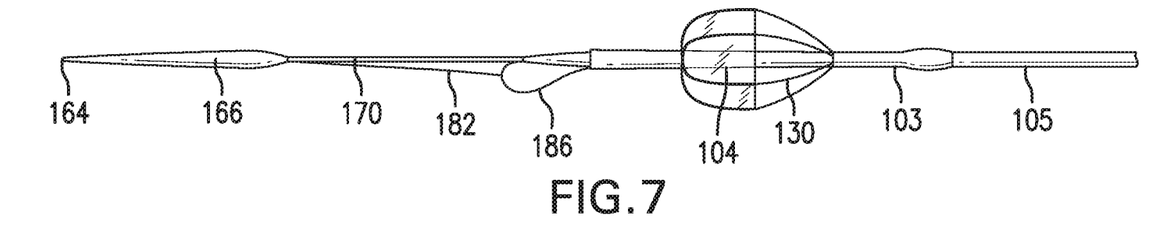
FIG. 7 illustrates the system of FIG. 6 in a deployed configuration.
Figure 8:
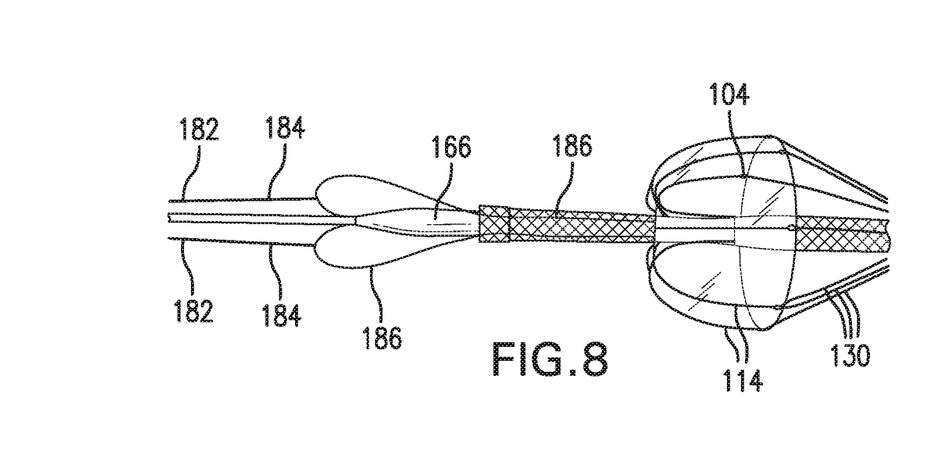
FIG. 8 illustrates a zoomed view of the system of FIG. 7.

The invention further comprises a method of delivering and deploying the temporary valve. The sheath 101 is advanced through the body to a target location in the inverted delivery configuration. Once at the target location, the dilator 160 is advanced distally in the direction 2, said distal movement being transferred to the first section 103 via the first and second wires 182, 184. As the dilator moves distal from the second section 105, the first section 103 everts to an elongated, non-folded configuration, as shown in FIGS. 7-8. As the valve body 104 exits the second section 105, the canopy 106 of the valve body 104 radially expands outward to an umbrella configuration. In embodiments without ribs 114, the radial expansion may be caused by the flow of blood therepast during diastole. In one embodiment, once the valve body 104 has been properly positioned in a target location, one free end 188 of the second wire 186 may be retracted in the direction 1 to remove the second wire 186 from the device 100 and out of the body. This retraction releases the second wire 186 from the first wire 182 and attachment location 190, thereby disconnecting the first section 103 from the dilator 160. The dilator 160 may then be removed from the device and from the body without affecting the position of the first section 103 and valve body 104. A catheter (e.g., balloon catheter, TAVI catheter, etc.) may then be inserted into the sheath 101 via the hemostatic valve 156 to perform a target procedure. Once the target procedure is completed, the valve body 104 and first section 103 must be removed from the body. Removal of the device 100 may be performed in a number of ways, each of which is described separately hereinafter. It is noted that the proximal retraction of the dilator 160 and the second wire 186 may be performed in any order depending on clinical convenience.

In a first method of removing the temporary valve, the device 100 is removed from the body with the valve body 104 in the umbrella or radially expanded canopy configuration. This method is especially expedient in an embodiment without ribs 114 as it reduces the additional time needed to perform a procedure. However, even in the embodiment including the ribs 114, the expanded valve body 104, due to its flexible construction, may be removed with a negligible amount of trauma to the patient vessel. In this embodiment, the lines 130 may be permanently fixed to attachment points 132 and no attachment wire 140 is needed.

In a second method of removing the temporary valve, the lines 130 of the valve body 104 are separated from the first section 103 to permit the valve body 104 to straighten for removal. Once a valve repair or replacement procedure is completed, one free end of the attachment wire 140 is pulled proximally, causing the second free end to be pulled through the device 100 and to release loops 134 of the lines 130, as shown sequentially in FIGS. 1-3. Once the lines 130 disengage from first section 103, proximal retraction of the device 100 causes the now free end 110 of the valve to move distally of the valve first end 108, as depicted in FIG. 3. The valve body will evert and straighten becoming substantially aligned with the axis of the first section 103. The optional ribs 114 may be biased to a straightened or substantially straightened configuration to aid in movement of the valve to the configuration shown, e.g., in FIG. 3 upon release of the lines, thereby reducing the outer profile of the valve and permitting withdrawal therefrom from the vessel without causing damage thereto.

Figure 9:
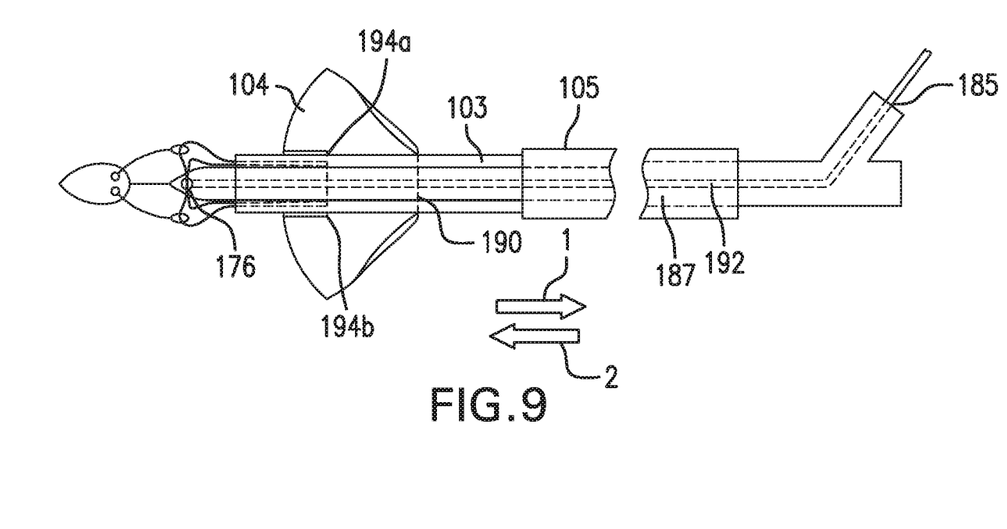
FIG. 9 illustrates a partial cross-sectional view of a sheath and temporary valve according to a first alternate embodiment in a deployed configuration.

In a third method of removing the temporary valve, as depicted in FIG. 9, the valve body 104 may be moved back to a folded configuration into the first section 103 for removal via an optional third wire 192. Specifically, the third wire 192 may be provided to control a reversible inversion and eversion of the first section and valve independently of the position of the dilator. The third wire 192 may extend through the dilator channel 187 from the proximal opening 185 and exit therefrom via distal opening 176 to connect directly to the first section in the same manner as the second wire 186. Specifically, the third wire 192 traverses the length of the central lumen of the dilator, extends out of the distal opening 176 of the dilator and moved proximally into the first section 103 toward the sheath attachment location 190, between an outer surface of the dilator 160 and an inner surface of said first section 103. The third wire 192 is then woven in and out of the first section 103 any plurality of times at the sheath attachment location 190. Specifically, the third wire 192 exits the first section 103 at attachment point 194a, extends 180 degrees about said sheath and subsequently reenters the first section 103 at attachment point 194b. The third wire 192 then completes a symmetric circuit, extending distally through the sheath, back into the distal opening 176, through the channel 187 and ends at the proximal opening 185 of the dilator. When the target procedure is completed, both free ends of the third wire 192 are pulled proximally in the direction 1 to cause the first section 103 to move proximally into the second section 105 and optionally become at least partially inverted within the second section. The inverted valve body 104, having a lower outer profile than the radially expanded valve, can then be removed from the body without damage or with minimal or negligible damage to a vessel wall. That is, in the straightened everted configuration of FIG. 3, the valve body 104 is more capable of being radially compressed to permit retraction through narrow vasculature.

In some embodiments, the device 100 may include the protective outer tube 107 extending over the second section 105 of the sheath 101, as depicted in FIGS. 1-3. The outer tube 107 may be provided to secure an optional wire tube 109 through which the attachment wire 140 may be received. The wire tube 109 may extend parallel to the second section 105 but may be located outside of the second section 105 and extending fully or partially coextensively thereto. In one embodiment, the distal end 111 of the wire tube 109 may be located proximal to the distal end 152 of second section 105 with the attachment wire 140 extending out of said distal end 111 and entering the first section 103 at the attachment point 132. This embodiment lends the advantage of maximizing an internal diameter of the second section 105 available for catheter insertion. In another embodiment, the wire tube 109 may be located inside the guide tube 105, thus minimizing an outer profile of the device. In yet another embodiment, the attachment wire 140 may be inserted through a channel formed in the side wall of the second section 105. In yet another embodiment, the outer tube 107 may be omitted, in which case the attachment wire 140 may run through the lumen of the guide tube 105.

The first section 103 may be formed of Nitinol, polymer or other known materials and has a braided construction formed of one or more braided members (e.g., fibers, wires, etc.). In an alternative embodiment, the first section 103 may be made of a non-braided construction such as a flexible tube formed of e.g., fabric or polymer. The second section 105 may be formed of a polymer or other suitable material. The valve canopy 106 may be formed of a thin, flexible and fluid-impervious polymer material such as an elastomeric polymer or any other polymer exhibiting these properties. In another embodiment, the valve canopy 106 may be formed of fabric, pericardium, a metallic sheet, or another flexible, fluid-impervious material. The ribs 114 may be formed at least partially of a radiopaque material to aid in visibility of the device during the percutaneous procedure. The ribs 114 may be formed of a substantially flexible metal, Titanium, Nitinol, or other metal known in the art. Alternatively, the ribs may be formed of a polymer material such as for example polyurethane. The material of the optional ribs is preferably stiffer than the material of the valve canopy. Lines 130 may be formed of suture material, fabric, metal or a polymer. In another embodiment, the lines 130 may be formed as a continuation of the ribs 114 and formed of the same material as said ribs 114. The attachment wire 140 may be formed of Nitinol, metal, string, fabric, a polymer or other suitable materials. The guide tube 105 and wire tube may be formed of a polymer or other known material and has a length selected to provide access to, for example, the proximal descending aorta, under percutaneous access with a proximal end thereof remaining external to the body and accessible to a cardiologist or other user.

Figure 10:
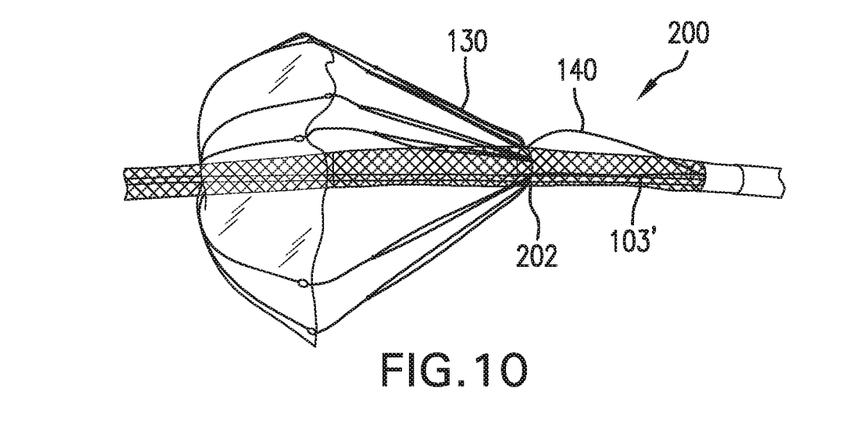
FIG. 10 illustrates a sheath and temporary valve according to a second alternate embodiment in a radially expanded canopy configuration.
Figure 11:
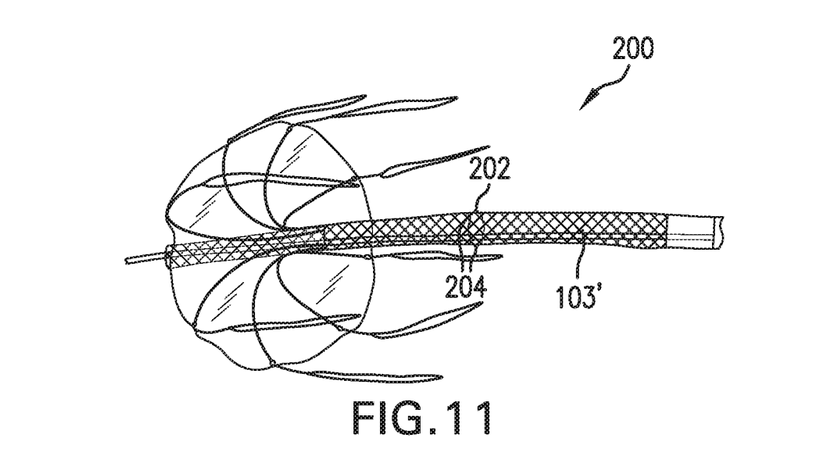
FIG. 11 illustrates the sheath and temporary valve of FIG. 10 during a detached configuration.
Figure 12:
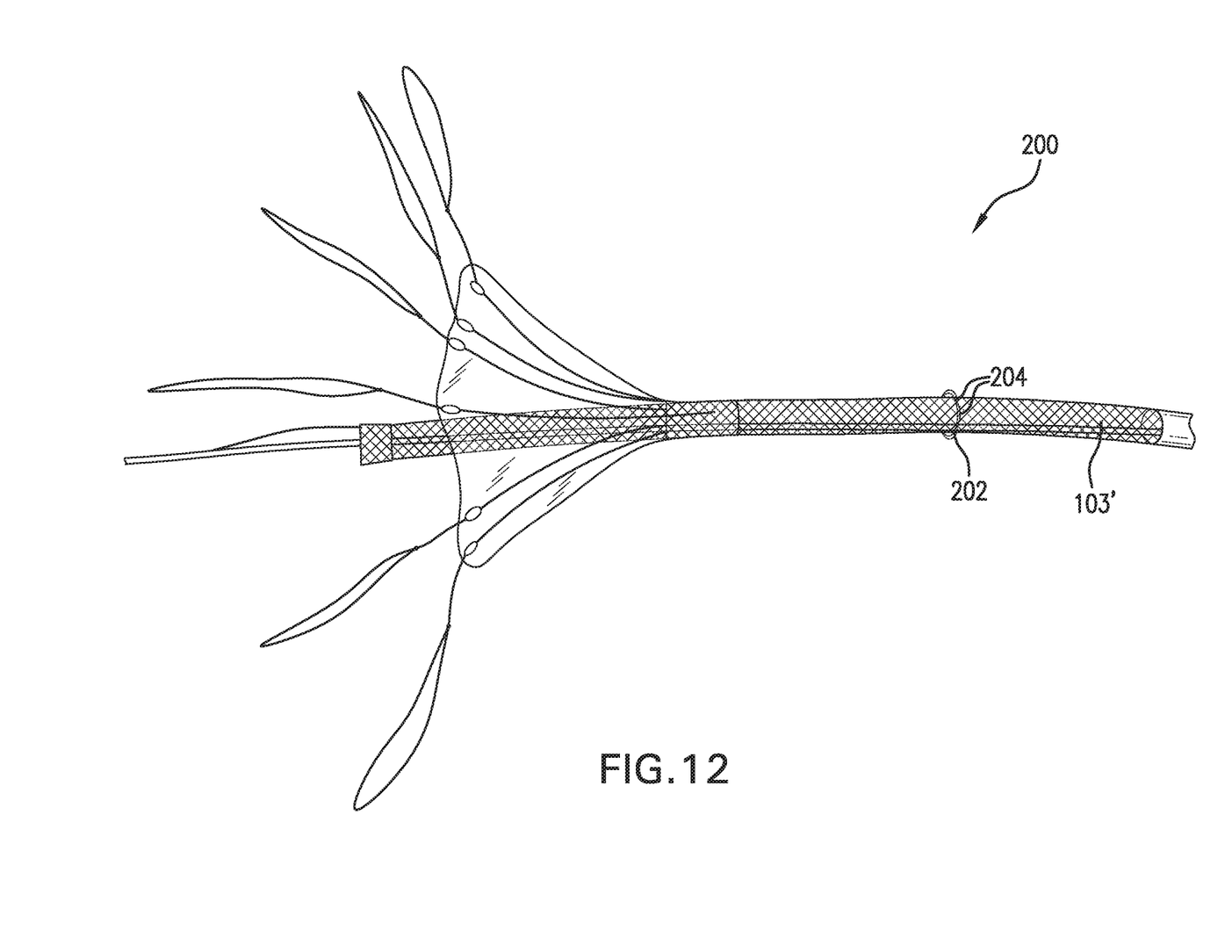
FIG. 12 illustrates the sheath and temporary valve of FIG. 10 during an everted configuration.

FIGS. 10-12 depict a device 200 according to an alternate embodiment. First section 103' of device 200 includes a ring 202 to which lines 130 are attached, the ring 202 comprised of a plurality of loops 204 permanently attached to first section 103' at attachment point 132 (e.g., see FIG. 10). In a preferred embodiment, the number of loops 204 corresponds to the number of lines 130, although any number of loops 204 may be provided without deviating from the scope of the invention. Whereas the attachment wire of FIGS. 1-5 is woven directly into the first section 103 to secure the lines 130 to the first section 103, the attachment wire 140 of FIGS. 10-12 is interwoven with ring 202 to secure the lines 130 to the first section. During a manufacturing or a pre-surgical step, the free end of the attachment wire 140 is sequentially woven through a first one of the loops 204 and a first one of the lines 130 and then through a second one of the loops 204 and a second one of the lines 130 and so on. This configuration prevents the attachment wire 140 from being caught on the first section 103 during removal thereof. The ring 202 may be formed of a single wire wound to form a number of loops or may be formed of a plurality of individual loops 204 secured to the first section 103. The ring 202 may be formed of wire, suture material, string or another suitable material.

It will be apparent to those of skill in the art that many variations, additions, modifications, and other applications may be made to what has been particularly shown and described herein by way of embodiments, without departing from the spirit or scope of the invention. For example, one or more features of the various embodiments disclosed herein may be combined in any combination. It is therefore intended that the scope of the invention, as defined by the claims, includes all foreseeable variations, additions, modifications or applications.

What is claimed is:

1. A temporary valve device, comprising:
a sheath having a first section and a second section, said first section attached to a distal end of said second section;
a temporary valve having a first valve end and a second valve end, said first valve end fixedly attached to an outer circumference of said first section of the sheath; and
an attachment mechanism detachably connecting said second valve end of said temporary valve to said outer circumference of the first section of the sheath.

2. The device of claim 1, wherein said first section is formed of a braided member.

3. The device of claim 1, wherein said temporary valve is formed with an umbrella shape.

4. The device of claim 3, wherein said temporary valve has an opening extending therethrough.

5. The device of claim 1, wherein said attachment mechanism comprises a plurality of lines connecting said second valve end to said first section.

6. The device of claim 5, wherein first ends of said lines are attached to a rim of said temporary valve.

7. The device of claim 5, wherein first ends of said lines are attached to a position separated from a rim of said temporary valve by a predetermined gap.

8. The device of claim 5, further comprising a plurality of reinforcing ribs coupled to said temporary valve, said ribs being disposed about the temporary valve.

9. The device of claim 8, wherein said ribs are one of embedded in the temporary valve, attached to an inner surface of the temporary valve and attached to an outer surface of the temporary valve.

10. The device of claim 8, wherein said ribs extend from respective first rib ends to respective second rib ends, said first rib ends being separated from said first valve end.

11. The device of claim 10, wherein said second rib ends are one of separated from said second valve end and aligned with said second valve end.

12. The device of claim 10, wherein said second rib ends include attachment rings for attachment to said lines.

13. The device of claim 8, wherein said device includes one of 4 ribs, 8 ribs and 16 ribs.

14. The device of claim 8, wherein said ribs are biased to a radially expanded configuration.

15. The device of claim 5, wherein said lines include loops for attachment to an attachment wire.

16. The device of claim 15, wherein said attachment wire is interwoven through said line loops and said first section, said interwoven portion extending 180 degrees about a circumference of said first section.

17. The device of claim 15, wherein said first section includes a plurality of sheath loops to which the line loops are attached via the attachment wire.

18. The device of claim 1, wherein the temporary valve is invertable.

19. The device of claim 1, wherein said attachment mechanism is one of an attachment wire, string and pin.

20. The device of claim 1, wherein said attachment mechanism couples the temporary valve directly to said first section.

21. A temporary valve device, comprising:
a sheath having a first section and a second section, said first section attached to a distal end of said second section;
a temporary valve attached to an outer surface of said first section, said temporary valve extending from a first valve end to a second valve end;
an attachment mechanism reversibly connecting said temporary valve to said first section; and
a first control wire extending through said valve device and having first and second free ends located outside of said valve device, wherein a proximal retraction of said first and second free ends moves said first section and temporary valve to an inverted delivery configuration.

22. A percutaneous temporary valve system, comprising:
a sheath having a first section and a second section, said first section attached to a distal end of said second section;
a temporary valve having a first valve end and a second valve end, wherein said first valve end is fixedly attached to an outer circumference of said first section of the sheath and said second valve end is detachably connected to the outer circumference of said first section of the sheath; and
a dilator for insertion through said valve device, said dilator having a nosecone at a distal end thereof.

23. The system of claim 22, further comprising a first wire having first and second free ends located outside of said valve device, wherein a proximal retraction of said first and second free ends moves said first section and temporary valve to an inverted delivery configuration.

24. The system of claim 23, wherein said first wire is woven through said dilator, out of a distal dilator opening thereof and through said first section at an attachment point.

25. The system of claim 24, wherein the dilator comprises a reduced diameter waist distally of said distal opening.

26. The system of claim 24, further comprising a second wire connected to said dilator, said second wire including wire loops for receiving said first wire.

27. The system of claim 26, further comprising a third wire coupled to said first section, said third wire controlling inversion and eversion of the first section independently of a position of said dilator.

28. The system of claim 26, wherein said temporary valve comprises a plurality of lines connecting said second valve end to said first section.

29. The system of claim 28, further comprising an attachment wire, wherein said lines include looped free ends for attachment to said first section via said attachment wire.

30. The system of claim 22, wherein said first section is formed of a braided member.

31. The system of claim 22, wherein said temporary valve is invertable.

32. A temporary valve device, comprising:
a sheath having a first section and a second section, said first section attached to a distal end of said second section;
an invertible temporary valve having a first valve end and a second valve end, said first valve end fixedly attached to an outer circumference of said first section of the sheath and said second valve end detachably connected to said outer circumference of said first section of the sheath; and
wherein said temporary valve is reversibly movable between an inverted delivery configuration and a deployed canopy configuration, wherein, in said delivery configuration, said first section is inverted into said second section and wherein in said deployed configuration, said first section is moved distally out of said second section to permit radial expansion of said temporary valve.

33. The device of claim 32, wherein said first section is formed of a braided member.

34. The device of claim 32, wherein said temporary valve is formed with an umbrella shape having an opening extending therethrough to house a delivery device.

35. The device of claim 32, wherein said temporary valve has a diameter which increases from a proximal end to a distal end.

36. The device of claim 32, wherein said temporary valve comprises a plurality of lines connecting said second valve end to said first section.

37. The device of claim 36, wherein first ends of said lines are attached to a rim of said temporary valve.

38. The device of claim 36, wherein first ends of said lines are attached to a position separated from a rim of said temporary valve by a predetermined gap.

39. The device of claim 36, further comprising an attachment wire, wherein said lines include line loops are free ends thereof for attachment to said first section via said attachment wire.

40. The device of claim 39, wherein said attachment wire is interwoven through said line loops and said first section, said interwoven portion extending 180 degrees about a circumference of said first section.

41. The device of claim 40, wherein said first section includes a plurality of sheath loops to which the line loops are attached via the attachment wire.

42. The device of claim 36, wherein said lines are removably attached to said first section.

43. The device of claim 32, further comprising a plurality of reinforcing ribs coupled to said temporary valve, said ribs being symmetrically disposed about the temporary valve.

44. The device of claim 43, wherein said ribs are one of embedded in the temporary valve, attached to an inner surface of the temporary valve, and attached to an outer surface of the temporary valve.

45. The device of claim 43, wherein said ribs extend from respective first rib ends to respective second rib ends, said first rib ends being separated from said first valve end.

46. The device of claim 45, wherein said second rib ends are one of separated from said second valve end and aligned with said second valve end.

47. The device of claim 45, wherein said second rib ends include attachment rings for attachment to said lines.

48. The device of claim 43, wherein said device includes one of 8 ribs and 16 ribs.

49. The device of claim 43, wherein said ribs are biased to a radially expanded configuration.

50. The device of claim 32, further comprising a first control wire extending through said valve device and having first and second free ends located outside of said valve device, wherein a proximal retraction of said first and second free ends moves said sheath and temporary valve to said inverted delivery configuration.

\* \* \* \* \*